US009097684B2

(12) United States Patent
Tomioka et al.

(10) Patent No.: US 9,097,684 B2
(45) Date of Patent: Aug. 4, 2015

(54) SPECIMEN INSPECTION APPARATUS

(71) Applicant: SEIKO EPSON CORPORATION, Tokyo (JP)

(72) Inventors: Hiroto Tomioka, Chino (JP); Satoshi Takenaka, Chino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 0 days.

(21) Appl. No.: 14/201,542

(22) Filed: Mar. 7, 2014

(65) Prior Publication Data

US 2014/0252231 A1 Sep. 11, 2014

(30) Foreign Application Priority Data

Mar. 8, 2013 (JP) ................................. 2013-046264

(51) Int. Cl.

| | |
|---|---|
| ***G01J 5/02*** | (2006.01) |
| ***G01N 21/89*** | (2006.01) |
| ***G01N 21/3581*** | (2014.01) |
| ***G01N 21/95*** | (2006.01) |

(52) U.S. Cl.

CPC ............ *G01N 21/89* (2013.01); *G01N 21/3581* (2013.01); *G01N 21/9508* (2013.01)

(58) Field of Classification Search

CPC ... G01N 21/3581; G01V 3/30; G02F 2203/13
USPC ............. 250/338.1–338.5, 340, 341.1–341.8
See application file for complete search history.

(56) References Cited

U.S. PATENT DOCUMENTS

| | | | | |
|---|---|---|---|---|
| 2006/0235621 | A1 | 10/2006 | Cole et al. | |
| 2008/0296501 | A1 * | 12/2008 | Breit et al. | 250/341.8 |
| 2009/0060128 | A1 * | 3/2009 | Kang et al. | 378/57 |
| 2013/0141115 | A1 * | 6/2013 | Bourely et al. | 324/637 |

FOREIGN PATENT DOCUMENTS

| | | | | | |
|---|---|---|---|---|---|
| EP | 2 042 855 | A1 | | 4/2009 | |
| JP | 2004117059 | A | * | 4/2004 | G01N 21/958 |
| JP | 2005-214954 | A | | 8/2005 | |
| JP | 2006-516722 | A | | 7/2006 | |
| JP | 2007-198802 | A | | 8/2007 | |
| JP | 2008-516639 | A | | 5/2008 | |
| JP | 2010-216890 | A | | 9/2010 | |
| JP | 2011117957 | A | * | 6/2011 | |
| JP | 2011-145215 | A | | 7/2011 | |
| JP | 2011-257179 | A | | 12/2011 | |
| WO | 2005/123569 | A2 | | 12/2005 | |
| WO | 2008/001785 | A1 | | 1/2008 | |

* cited by examiner

*Primary Examiner* — Kiho Kim
(74) *Attorney, Agent, or Firm* — Maschoff Brennan

(57) ABSTRACT

A specimen inspection apparatus includes: a terahertz wave generation unit which generates a terahertz wave; a transportation unit which includes a transportation surface on which specimens as inspection objects are loaded and is configured so as to transport the specimens in an in-plane direction of the transportation surface; an irradiation direction changing unit which changes an irradiation direction of a terahertz wave which is emitted from the terahertz wave generation unit and is emitted to the specimens loaded on the transportation surface; and a terahertz wave detection unit which detects a terahertz wave which is emitted to the specimens loaded on the transportation surface to transmit therethrough or be reflected thereby, wherein the irradiation direction changing unit changes the irradiation direction by changing a position of the terahertz wave generation unit.

7 Claims, 12 Drawing Sheets

30
54
100
50
52
12
4
10
Z
Y
X
40
54

30
54
100
50
52
12
2
10
Z
Y
X
40
54

SPECIMEN INSPECTION APPARATUS

BACKGROUND

1. Technical Field

The present invention relates to a specimen inspection apparatus.

2. Related Art

In recent years, a terahertz wave which is an electromagnetic wave having a frequency of 100 GHz to 30 THz has attracted attention. The terahertz wave can be used in imaging, various measurements such as spectroscopic measurement, non-destructive testing, and the like.

For example, Pamphlet of International Publication No. 2008/1785 discloses a specimen inspection apparatus which irradiates a medicine (specimen) with a terahertz wave and inspects whether or not foreign materials are contained in the medicine, based on the terahertz wave transmitting through or reflected by the medicine.

However, the specimen inspection apparatus of Pamphlet of International Publication No. 2008/1785 irradiates the medicine with the terahertz wave only from one direction. Accordingly, in the specimen inspection apparatus of Pamphlet of International Publication No. 2008/1785, the terahertz wave is significantly scattered depending on a shape or a disposed state of the medicine, and detection precision may be decreased. Specifically, in a case where the medicine is printed, the terahertz wave is significantly scattered and the detection precision may be decreased.

SUMMARY

An advantage of some aspects of the invention is to provide a specimen inspection apparatus which can suppress a decrease in detection precision due to scattering of a terahertz wave.

An aspect of the invention is directed to a specimen inspection apparatus including: a terahertz wave generation unit which generates a terahertz wave; a transportation unit which includes a transportation surface on which specimens as inspection objects are loaded and is configured so as to transport the specimens in an in-plane direction of the transportation surface; an irradiation direction changing unit which changes an irradiation direction of a terahertz wave which is emitted from the terahertz wave generation unit and is emitted to the specimens loaded on the transportation surface; and a terahertz wave detection unit which detects a terahertz wave which is emitted to the specimens loaded on the transportation surface to transmit therethrough or be reflected thereby, in which the irradiation direction changing unit changes the irradiation direction by changing a position of the terahertz wave generation unit.

According to the specimen inspection apparatus, it is possible to emit the terahertz wave to the specimens by avoiding an irradiation direction in which the scattering of the terahertz wave is great. Accordingly, the specimen inspection apparatus can suppress the decrease in detection precision due to the scattering of the terahertz wave.

The specimen inspection apparatus according to the aspect of the invention may further include a detection position control unit which controls a position of the terahertz wave detection unit so as to detect the terahertz wave along the irradiation direction.

According to the specimen inspection apparatus with this configuration, it is possible to obtain high detection precision.

Another aspect of the invention is directed to a specimen inspection apparatus including: a terahertz wave generation unit which generates a terahertz wave; a transportation unit which includes a transportation surface on which specimens as inspection objects are loaded and is configured so as to transport the specimens in an in-plane direction of the transportation surface; an irradiation direction changing unit which changes an irradiation direction of a terahertz wave which is emitted from the terahertz wave generation unit and is emitted to the specimens loaded on the transportation surface; and a terahertz wave detection unit which detects a terahertz wave which is emitted to the specimens loaded on the transportation surface to transmit therethrough or be reflected thereby, in which the irradiation direction changing unit includes reflection units which can reflect the terahertz wave emitted from the terahertz wave generation unit, and changes the irradiation direction by changing positions of the reflection units.

According to the specimen inspection apparatus, it is possible to easily suppress the decrease in detection precision due to the scattering of the terahertz wave by moving the reflection units.

In the specimen inspection apparatus according to the aspect of the invention, the transportation unit may be configured so as to arrange the specimens so that the specimens are not superimposed on each other when seen from the irradiation direction.

According to the specimen inspection apparatus with this configuration, it is possible to emit terahertz waves having the same intensity to each of the plurality of specimens.

In the specimen inspection apparatus according to the aspect of the invention, the terahertz wave generation unit may include an optical pulse generation unit which generates an optical pulse, and a photoconductive antenna which is irradiated with the optical pulse generated by the optical pulse generation unit.

According to the specimen inspection apparatus with this configuration, it is possible to suppress the decrease in detection precision due to the scattering of the terahertz wave.

The specimen inspection apparatus according to the aspect of the invention may further include: an irradiation direction determination unit which determines the irradiation direction based on the terahertz wave detected by the terahertz wave detection unit; and an irradiation direction control unit which controls the irradiation direction changing unit based on the determination of the irradiation direction determination unit.

According to the specimen inspection apparatus with this configuration, it is possible to suppress the decrease in detection precision due to the scattering of the terahertz wave.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, preferred embodiments of the invention will be described in detail with reference to the drawings. The embodiments which will be described hereinafter do not unduly limit the content of the invention of the aspects. All configurations which will be described hereinafter are not limited to be compulsory constituent elements of the invention.

1. First Embodiment

1.1. Configuration

Figure 1:
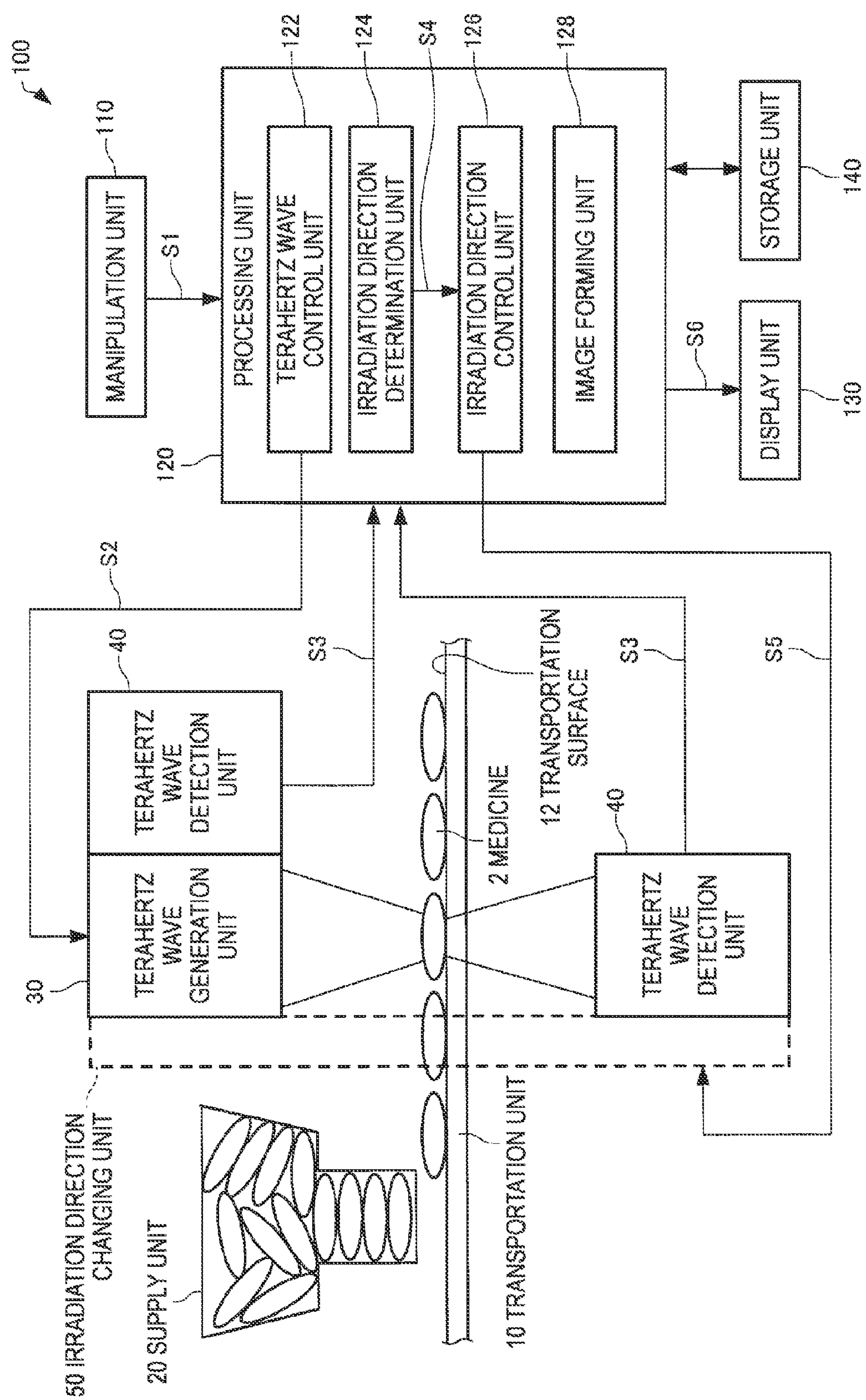
FIG. 1 is a diagram schematically showing a specimen inspection apparatus according to a first embodiment.
Figure 2:
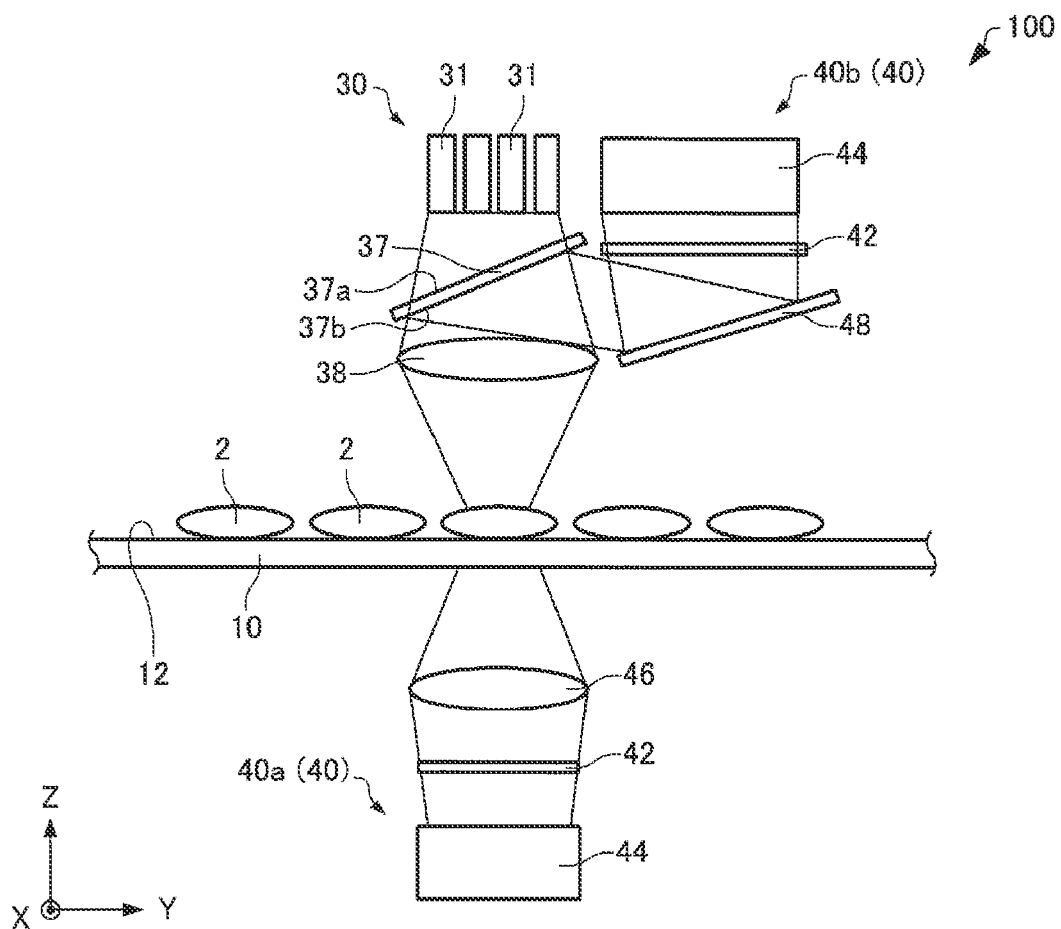
FIG. 2 is a diagram schematically showing a part of a specimen inspection apparatus according to a first embodiment.

First, a specimen inspection apparatus according to a first embodiment will be described with reference to the drawings. FIG. 1 is a diagram schematically showing a specimen inspection apparatus 100 according to the first embodiment. FIG. 2 is a diagram schematically showing a part of the specimen inspection apparatus 100 according to the first embodiment. For convenience, an irradiation direction changing unit 50 is perspectively shown in FIG. 1. In FIG. 2 and FIGS. 3, 4, 7, and 8, which will be described later, an X axis, a Y axis, and a Z axis are shown as three axes intersecting each other.

Hereinafter, the specimen inspection apparatus 100 for inspecting a medicine 2 as a specimen which is an inspection object will be described. Printing for displaying a name of a medicine, for example, is formed on the medicine 2.

As shown in FIGS. 1 and 2, the specimen inspection apparatus 100 includes a transportation unit 10, a terahertz wave generation unit 30, a terahertz wave detection unit 40, and an irradiation direction changing unit 50. The specimen inspection apparatus 100 can further include a supply unit 20, a manipulation unit 110, a processing unit 120, a display unit 130, and a storage unit 140.

The transportation unit 10 is configured so as to transport the medicine 2. The aspect of the transportation unit 10 is not limited as long as it can transport the medicine 2, and may be a belt conveyer. The transportation unit 10 includes a transportation surface 12 on which the medicine 2 is loaded. In the example shown in the drawing, the transportation surface 12 is a flat surface and is perpendicular along the Z axis (not shown). The transportation unit 10 transports the medicine 2 in an in-plane direction of the transportation surface 12. In the example shown in the drawing, the transportation unit 10 transports the medicine 2 in a Y axis direction.

Although not shown in the drawing, a recess may be formed on the transportation surface 12 and the medicine 2 may be disposed in the recess. Accordingly, in a case where an impact is applied to the transportation unit 10 during the transportation of the medicine 2, for example, it is possible to suppress deviation of the medicine 2 from a predetermined position.

Figure 3:
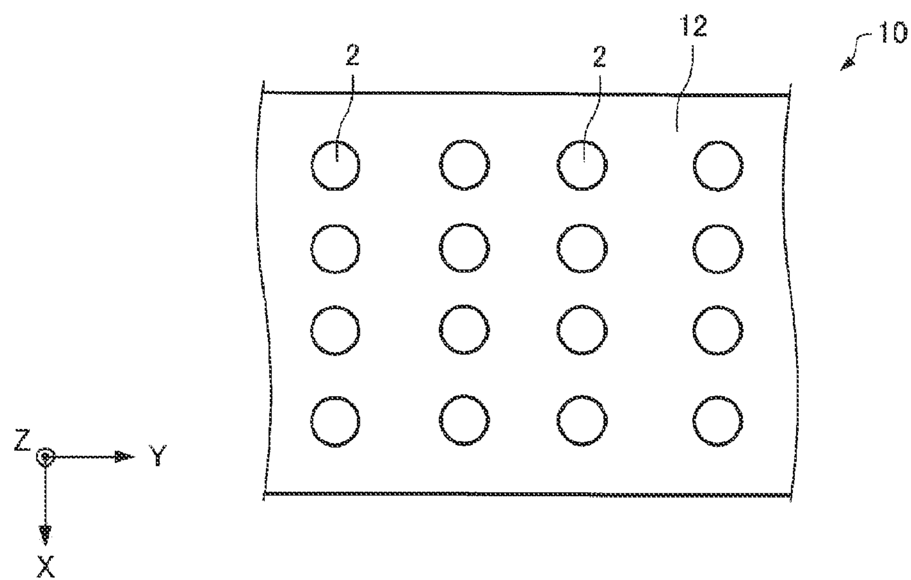
FIG. 3 is a diagram schematically showing a transportation unit of a specimen inspection apparatus according to a first embodiment.

The plurality of medicines 2 are loaded on the transportation surface 12 of the transportation unit 10. Herein, FIG. 3 is a diagram schematically showing the transportation unit 10 and is a diagram when seen from a Z axis direction. In the example shown in FIG. 3, the plurality of medicines 2 are loaded in a matrix in an X axis direction and the Y axis direction. For example, by supplying the plurality of medicines 2 to the transportation surface 12 on which recesses are formed, and vibrating the transportation unit 10 to dispose the medicines 2 in the recesses, it is possible to dispose the medicines 2 in predetermined positions on the transportation surface 12.

Figure 4:
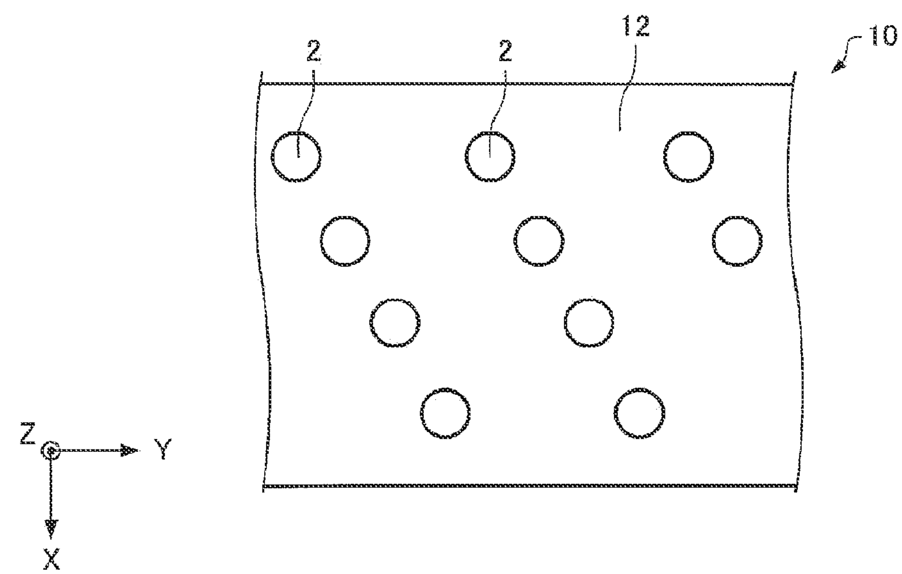
FIG. 4 is a diagram schematically showing a transportation unit of a specimen inspection apparatus according to a first embodiment.

As shown in FIG. 4, the plurality of medicines 2 may be disposed so as not to be superimposed on each other in the X axis direction. Accordingly, in a case where a terahertz wave is emitted in the X axis direction from the terahertz wave generation unit 30, it is possible to irradiate each of the plurality of medicines 2 with the terahertz waves having the equivalent intensity. As described above, the transportation unit 10 is preferably configured so as to dispose the medicines 2 so that the medicines 2 are not superimposed on each other when seen from an irradiation direction of the terahertz waves.

The transportation unit 10 enables the terahertz wave to transmit therethrough. A material of the transportation unit 10 is a thermoplastic resin such as polyethylene, polystyrene, polyamide, or polyimide, or a thermosetting resin such as polyurethane. The transportation unit 10 may be configured with paper or cloth.

When a refractive index of the material configuring the transportation unit 10 is set to n, and a wavelength of the terahertz wave incident to (emitted from the terahertz wave generation unit 30) the transportation unit 10 is set to $\lambda$, a thickness (size in the Z axis direction in the example shown in the drawing) t of the transportation unit 10 preferably satisfies a relationship of $t<(\lambda/n)$. In detail, in a case where the frequency of the terahertz wave incident to the transportation unit 10 is equal to or more than 300 GHz and equal to or less than 3 THz, it is preferable to satisfy a relationship of $t<(100/n)$ μm. When the relationship described above is not satisfied, the terahertz wave incident to the transportation unit 10 generates interference between an upper surface (transportation surface 12) and a lower surface of the transportation unit 10, and detection precision of the specimen inspection apparatus 100 may be decreased.

The "interference" is a phenomenon in which the terahertz wave reflected by the lower surface of the transportation unit and the terahertz wave reflected by the upper surface of the transportation unit generate interference to each other and the intensity is increased if phases of the terahertz waves coincide with each other and the intensity is decreased if the phases thereof do not coincide with each other.

As shown in FIG. 1, the supply unit 20 supplies the medicines 2 to the transportation surface 12 of the transportation unit 10. An aspect of the supply unit 20 is not particularly limited as long as it can supply the medicines 2 to the transportation surface 12, and is a funnel in the example shown in the drawing. A material of the supply unit 20 is glass, ceramics, or a resin, for example.

The terahertz wave generation unit 30 generates the terahertz wave. The "terahertz wave" is an electromagnetic wave having a frequency of 100 GHz to 30 THz, particularly an electromagnetic wave having a frequency of 300 GHz to 3 THz. As shown in FIG. 2, the terahertz wave generation unit 30 includes a light source 31, a half mirror 37, and a first lens 38.

Figure 5:
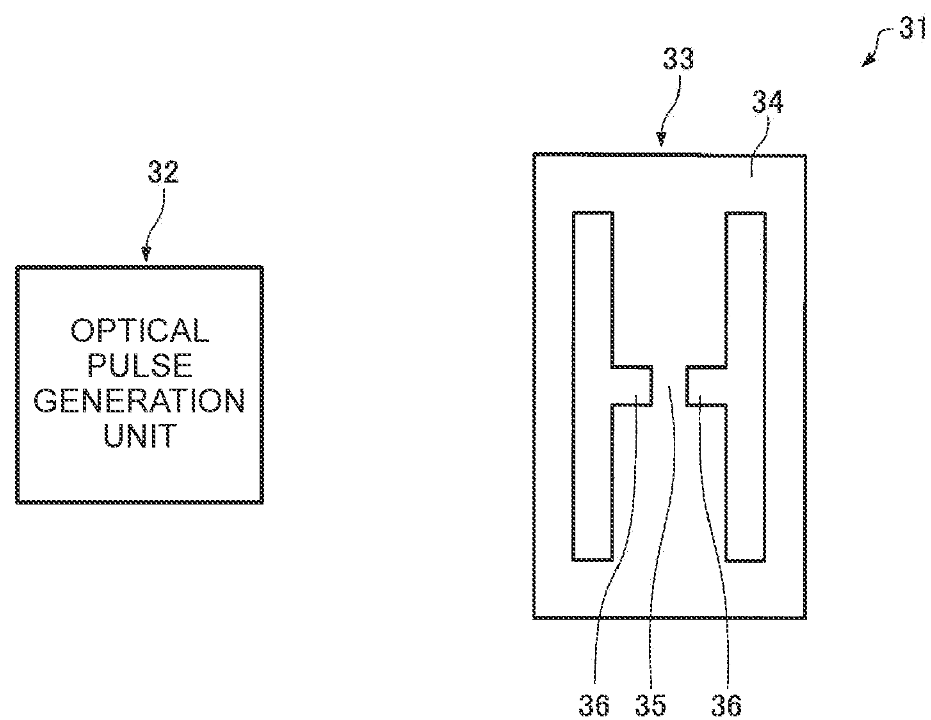
FIG. 5 is a diagram schematically showing a light source of a terahertz wave generation unit of a specimen inspection apparatus according to a first embodiment.

As shown in FIG. 2, a plurality of light sources 31 may be provided. Herein, FIG. 5 is a diagram schematically showing the light source 31 of the terahertz wave generation unit 30. As shown in FIG. 5, the light source 31 includes an optical pulse generation unit 32 and a photoconductive antenna 33.

The optical pulse generation unit 32 generates an optical pulse which is an excitation light. The "optical pulse" is light in which intensity sharply changes in a short time. A pulse width (full-width at half-maximum FWHM) of the optical pulse is, for example, equal to or more than 1 fs (femtosecond) and equal to or less than 800 fs.

As the optical pulse generation unit 32, a semiconductor laser including a pulse compression unit formed of a semiconductor material, a femtosecond fiber laser, or a titanium-sapphire laser is used, for example. Particularly, the semiconductor laser can be miniaturized and therefore can be preferably used as the optical pulse generation unit 32.

The photoconductive antenna 33 is irradiated with the optical pulse generated by the optical pulse generation unit 32 and accordingly generates the terahertz wave. In the example shown in the drawing, the photoconductive antenna 33 is a dipole-shaped photoconductive antenna (PCA). The photoconductive antenna 33 includes a substrate 34 which is a semiconductor substrate, and a pair of electrodes 36 which are provided on the substrate 34 and are disposed to face each other with a gap 35 interposed therebetween. When the optical pulse is emitted between the electrodes 36, the photoconductive antenna 33 generates the terahertz wave.

The substrate 34 includes, for example, a semi-insulating GaAs (SI-GaAs) substrate and a low temperature growth GaAs (LT-GaAs) layer which is provided on the SI-GaAs substrate. A material of the electrodes 36 is gold, for example. A distance between the pair of electrodes 36 is not particularly limited and is suitably set according to conditions, but is equal to or greater than 1 μm or equal to or smaller than 10 μm.

In the light source 31, first, the optical pulse generation unit 32 generates the optical pulse and emits the optical pulse towards the gap 35 of the photoconductive antenna 33. By emitting the optical pulse to the gap 35, free electrons are excited in the photoconductive antenna 33. Then, movement of the free electrons is accelerated by applying a voltage between the electrodes 36. Accordingly, the terahertz wave is generated.

The light source 31 is not limited to have a configuration of including the optical pulse generation unit 32 and the photoconductive antenna 33, and a quantum cascade laser or a difference frequency generation system using a non-linear optical crystal may be used, as the light source 31, for example.

As shown in FIG. 2, the terahertz wave emitted from the light source 31 is incident to a first surface 37*a* of the half mirror 37. The half mirror 37 enables the terahertz wave emitted from the light source 31 to transmit therethrough. In addition, the terahertz wave which is reflected by the medicine 2 is incident to a second surface 37*b* of the half mirror 37. The half mirror 37 can reflect the terahertz wave reflected by the medicine 2, towards a mirror 48 of the terahertz wave detection unit 40. As described above, the half mirror 37 is a half mirror which causes the terahertz wave incident from the first surface 37*a* to transmit therethrough and reflects the terahertz wave incident from the second surface 37*b*. In the example shown in the drawing, the first surface 37*a* and the second surface 37*b* face opposite directions. The half mirror 37 is configured with a laminated body of a glass plate and a metallic film, for example.

The terahertz wave transmitting through the half mirror 37 is incident to the first lens 38. The first lens 38 can concentrate the terahertz wave transmitting through the half mirror 37 to emit the terahertz wave to the transportation unit 10 side. In addition, the terahertz wave reflected by the medicine 2 is incident to the first lens 38. The first lens 38 can concentrate the terahertz wave reflected by the medicine 2 to emit the terahertz wave to the half mirror 37 side. A material of the first lens 38 is glass, for example. It is possible to efficiently introduce the terahertz wave to the medicine 2 or to the half mirror 37 by the first lens 38.

As shown in FIG. 2, the terahertz wave detection unit 40 detects the terahertz wave which is emitted to the medicine 2 loaded on the transportation surface 12 to transmit or be reflected. The terahertz wave detection unit 40 includes a filter 42, a detection unit 44, a second lens 46, and the mirror 48.

The filter 42 causes the terahertz wave having a target wavelength to transmit therethrough. A material of the filter 42 is metal, for example. Herein, FIG. 6 is a diagram schematically showing the filter 42 and the detection unit 44 of the terahertz wave detection unit 40.

Figure 6:
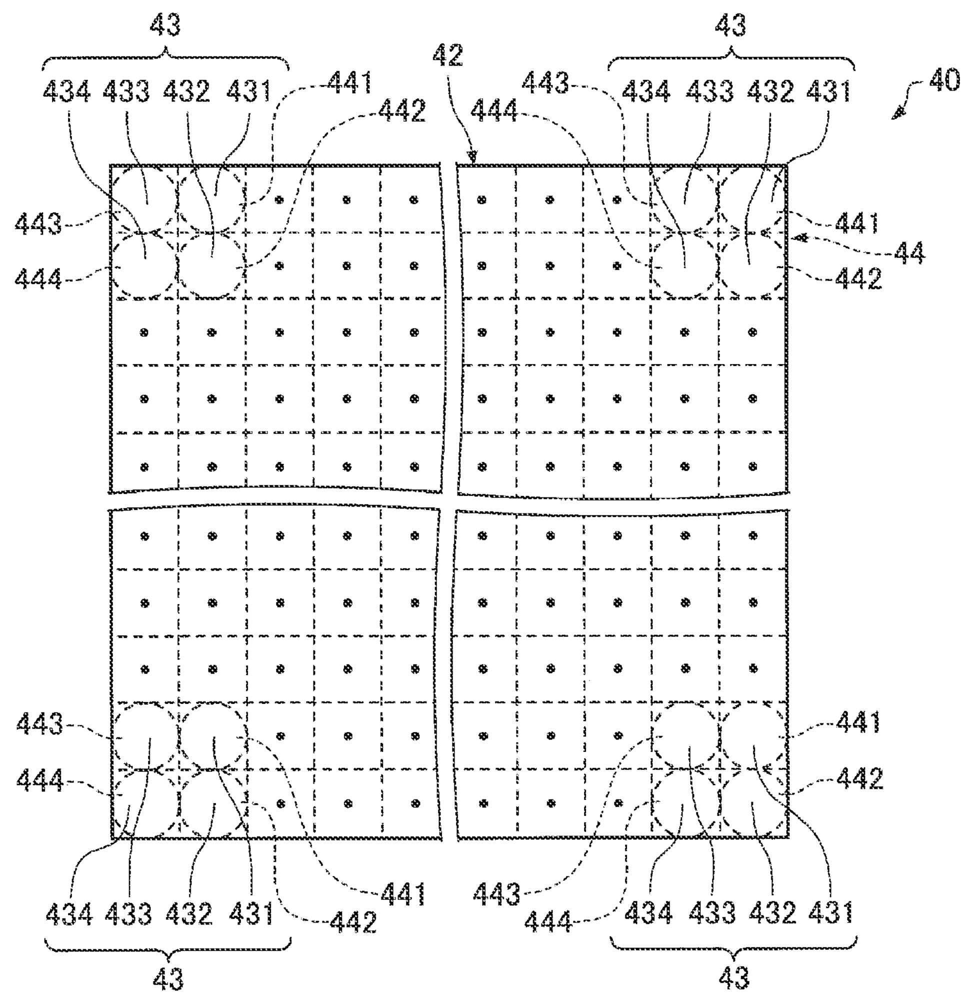
FIG. 6 is a diagram schematically showing a terahertz wave detection unit of a specimen inspection apparatus according to a first embodiment.

As shown in FIG. 6, the filter 42 includes a plurality of pixels (unit filter unit) 43 disposed two-dimensionally. The plurality of pixels 43 are disposed in a matrix. Each of the pixels 43 includes a plurality of regions for passing through the terahertz waves having different wavelengths from each other, that is, a plurality of regions in which the wavelengths of the terahertz waves passing through (hereinafter, also referred to as "pass wavelengths") are different from each other. In the example shown in the drawing, each of the pixels 43 includes a first region 431, a second region 432, a third region 433, and a fourth region 434.

As the detection unit 44, a unit which detects the terahertz wave by converting the terahertz wave into heat, that is, a unit which can detect energy (intensity) of the terahertz wave by converting the terahertz wave into heat is used, for example. In detail, the detection unit 44 is a pyroelectric sensor or a bolometer.

The detection unit 44 detects the terahertz wave having a target wavelength and which is transmitted through the filter 42. The detection unit 44 includes a first unit detection unit 441, a second unit detection unit 442, a third unit detection unit 443, and a fourth unit detection unit 444 provided corresponding to the first region 431, the second region 432, the third region 433, and the fourth region 434 of the pixel 43, respectively. The first unit detection unit 441, the second unit detection unit 442, the third unit detection unit 443, and the fourth unit detection unit 444 detect the terahertz wave passing through the first region 431, the second region 432, the third region 433, and the fourth region 434 of the pixel 43, respectively, by converting the terahertz wave into heat. Accordingly, in each of the pixels 43, it is possible to reliably detect terahertz waves having four target wavelengths.

As shown in FIG. 2, the plurality of terahertz wave detection units 40 may be provided. In the example shown in the drawing, the specimen inspection apparatus 100 includes a first terahertz wave detection unit 40*a* and a second terahertz wave detection unit 40*b*, as the terahertz wave detection unit 40.

The first terahertz wave detection unit 40*a* detects the terahertz wave which is emitted to and transmitted through the medicine 2. In the example shown in the drawing, the first terahertz wave detection unit 40*a* is positioned in the Z axis direction of the terahertz wave generation unit 30 and the transportation unit 10 is positioned between the first terahertz wave detection unit 40*a* and the terahertz wave generation unit 30.

The first terahertz wave detection unit 40*a* includes the second lens 46. The terahertz wave transmitting through the medicine 2 is incident to the second lens 46. The second lens 46 can concentrate the terahertz wave transmitting through the medicine 2 to emit the terahertz wave to the filter 42 side. A material of the second lens 46 is glass, for example. It is possible to efficiently introduce the terahertz wave to the filter 42 by the second lens 46.

The second terahertz wave detection unit 40*b* detects the terahertz wave emitted to and reflected by the medicine 2. In the example shown in the drawing, the second terahertz wave detection unit 40*b* is positioned in the Y axis direction of the terahertz wave generation unit 30 and is positioned on the same side as the terahertz wave generation unit 30 with respect to the transportation unit 10. In detail, both of the second terahertz wave detection unit 40*b* and the terahertz wave generation unit 30 are positioned in the positive Z axis direction of the transportation unit 10.

The second terahertz wave detection unit 40*b* includes the mirror 48. The terahertz wave reflected by the half mirror 37 is incident to the mirror 48. The mirror 48 reflects the terahertz wave reflected by the half mirror 37, towards the filter 42. That is, it is possible to introduce the terahertz wave reflected by the medicine 2 to the filter 42 of the second terahertz wave detection unit 40*b* by the half mirror 37 and the mirror 48. A material of the mirror 48 is glass or metal, for example.

In the specimen inspection apparatus 100, it is possible to select inspection to be performed using the first terahertz wave detection unit 40*a* or inspection to be performed using the second terahertz wave detection unit 40*b*, depending on the shape or the material of the medicine 2. That is, in a case where the intensity of the terahertz wave which is emitted to and transmitted through the medicine 2 is strong, the inspection is performed using the first terahertz wave detection unit 40*a*, and in a case where the intensity of the terahertz wave which is emitted to and reflected by the medicine 2 is strong, the inspection is performed using the second terahertz wave detection unit 40*b*. By using both of the terahertz wave detection units 40*a* and 40*b*, both the terahertz wave transmitting through the medicine 2 and the terahertz wave reflected by the medicine 2 may be detected at the same time.

Figure 7:
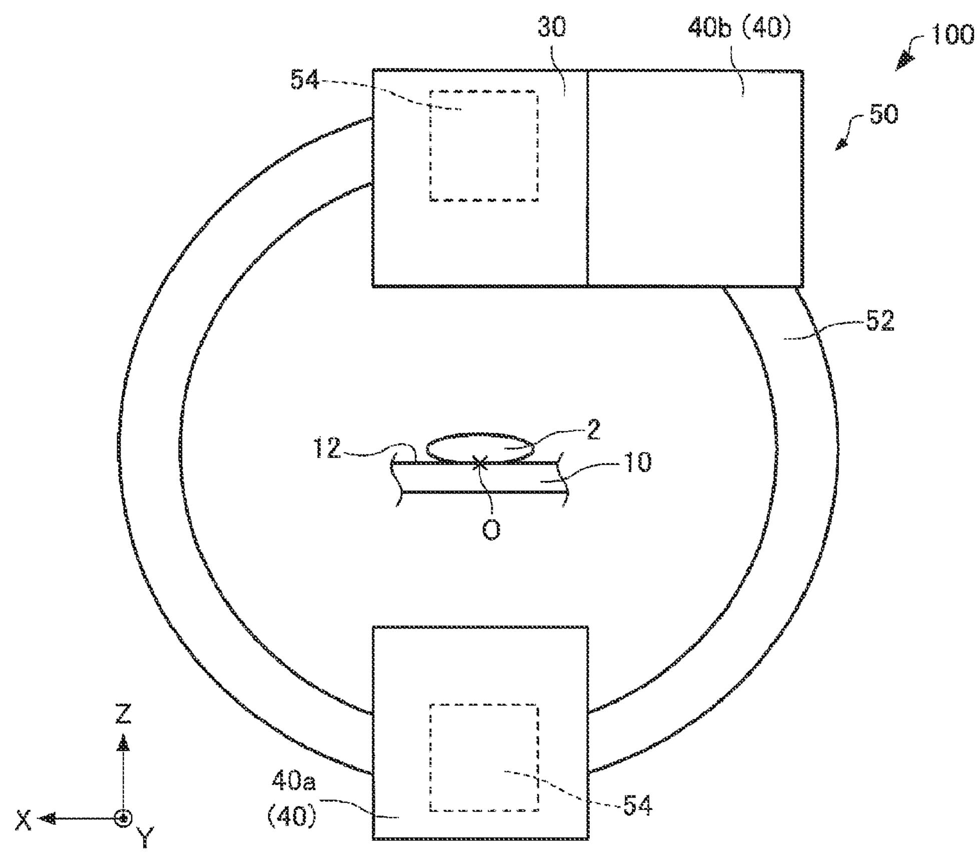
FIG. 7 is a diagram schematically showing a part of a specimen inspection apparatus according to a first embodiment.
Figure 8:
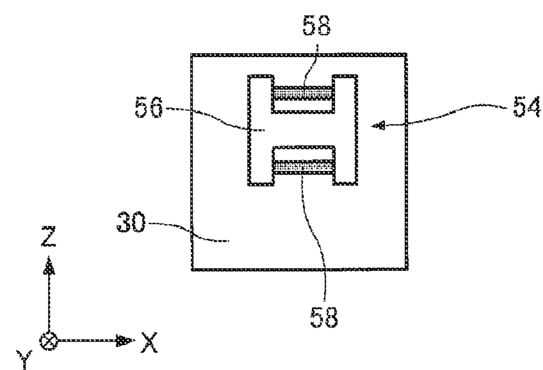
FIG. 8 is a diagram schematically showing a movable unit of an irradiation direction changing unit of a specimen inspection apparatus according to a first embodiment.

As shown in FIG. 1, the irradiation direction changing unit 50 supports the terahertz wave generation unit 30 and the terahertz wave detection unit 40. Herein, FIG. 7 is a diagram schematically showing a part of the specimen inspection apparatus 100 and is a diagram when seen from a transportation direction (Y axis direction) of the transportation unit 10. FIG. 8 is a diagram schematically showing the movable unit 54 of the irradiation direction changing unit 50 and is a diagram when seen from the Y axis direction (opposite direction from the direction of FIG. 7). For convenience, in FIG. 7, the terahertz wave generation unit 30 and the terahertz wave detection unit 40 are shown in a simplified manner. In FIG. 8, the terahertz wave generation unit 30 is shown in a simplified manner.

The irradiation direction changing unit 50 changes the position of the terahertz wave generation unit 30. Accordingly, an irradiation direction of the terahertz wave which is emitted from the terahertz wave generation unit 30 and emitted to the medicine 2 loaded on the transportation surface 12 can be changed. In addition, the irradiation direction changing unit 50 can change the position of the terahertz wave detection units 40. As shown in FIGS. 7 and 8, the irradiation direction changing unit 50 includes a rail 52 and the movable unit 54.

The rail 52 is provided on a periphery of the transportation unit 10. As shown in FIG. 7, the rail 52 may be a member having a circular shape in an XZ plane, and the transportation unit 10 may be extended in the Y axis direction through the inside of the rail 52. In the example shown in the drawing, a shape of the rail 52 is a circle having a point overlapped with the transportation surface 12 as a center O. The shape of the rail 52 is not limited to the example shown in the drawing and may be a triangle or a rectangle. In addition, the shape of the rail 52 may be a circle having a center of gravity of the medicine 2 as a center O. The rail 52 may be continuously provided on the periphery of the transportation unit 10 as shown in FIG. 7, or may be provided with a part thereof separated. A material of the rail 52 is metal or a resin, for example.

The movable unit 54 is positioned on the rail 52 and supports the terahertz wave generation unit 30 and the terahertz wave detection unit 40. The movable unit 54 can move along the rail 52. The terahertz wave generation unit 30 and the first terahertz wave detection unit 40*a* can be moved according to the movement of the movable unit 54.

The plurality of movable units 54 are provided. In the example shown in the drawing, two movable units 54 are provided corresponding to the terahertz wave generation unit 30 and the first terahertz wave detection unit 40*a*. The terahertz wave generation unit 30 and the second terahertz wave detection unit 40*b* are connected to each other through a connection member (not shown), for example. Accordingly, the second terahertz wave detection unit 40*b* can be moved according to the movement of the terahertz wave generation unit 30.

Although not shown in the drawing, the terahertz wave generation unit 30 and the second terahertz wave detection unit 40*b* are not connected to each other, and the movable units 54 may be provided so as to correspond to the terahertz wave generation unit 30 and each of the terahertz wave detection units 40*a* and 40*b*. In this case, three movable units 54 are provided.

The movable unit 54 supporting the terahertz wave generation unit 30 and the movable unit 54 supporting the first terahertz wave detection unit 40*a* may be movable so as to be symmetric with respect to the center O. Accordingly, it is possible to efficiently introduce the terahertz wave transmitting through the medicine 2 to the first terahertz wave detection unit 40*a*.

As shown in FIG. 8, the movable unit 54 includes a support base 56 and wheels 58. The support base 56 supports the terahertz wave generation unit 30 or the first terahertz wave detection unit 40*a*. The wheels 58 support the support base 56 and come in contact with the rail 52. The wheels 58 can be smoothly rotated on the rail 52. A material of the support base 56 and the wheels 58 is metal or a resin, for example.

The movable unit 54 can support the terahertz wave generation unit 30 and the terahertz wave detection unit 40, and a shape thereof is not limited to the example shown in the drawing, as long as it is movable along the rail 52.

As shown in FIG. 1, the manipulation unit 110 acquires a manipulation signal based on manipulation by a user and performs a process for transmitting the manipulation signal to the processing unit 120. The manipulation unit 110 is a touch panel-type display, button, keys, or a microphone, for example.

The processing unit (CPU) 120 performs various calculation processes based on data acquired from the terahertz wave detection unit 40 or various control processes (control of the terahertz wave generation unit 30 and the irradiation direction changing unit 50, or display control with respect to the display unit 130), based on a program stored in the storage unit 140. In detail, by executing the program stored in the storage unit 140, the processing unit 120 functions as a terahertz wave control unit 122, an irradiation direction determination unit 124, an irradiation direction control unit 126, and an image forming unit 128.

The terahertz wave control unit 122 performs control of the terahertz wave generation unit 30. In detail, the terahertz wave control unit 122 transmits a driving signal S2 to the terahertz wave generation unit 30 based on a signal S1 input from the manipulation unit 110.

The irradiation direction determination unit 124 determines the irradiation direction of the terahertz wave. In detail, the irradiation direction determination unit 124 determines the irradiation direction of the terahertz wave emitted from the terahertz wave generation unit 30, based on a detection signal S3 originated from the terahertz wave detected by the terahertz wave detection unit 40.

The irradiation direction control unit 126 controls the irradiation direction changing unit 50. In detail, the irradiation direction control unit 126 transmits a driving signal S5 to the movable unit 54 of the irradiation direction changing unit 50, based on the signal S1 input from the manipulation unit 110 or a signal S4 input from the irradiation direction determination unit 124. By controlling the irradiation direction changing unit 50, the irradiation direction control unit 126 controls the position of the terahertz wave generation unit 30 and controls the position of the terahertz wave detection unit 40. That is, the irradiation direction control unit 126 is also a detection position control unit which controls the position of the terahertz wave detection unit 40.

The image forming unit 128 creates image data of an image showing distribution of materials contained in the medicine 2, based on the detection signal S3 from the terahertz wave detection unit 40.

The display unit 130 displays processed results of the processing unit 120 as characters, graphs, or other information, based on a display signal S6 input from the processing unit 120. In detail, the display unit 130 displays the image data created by the image forming unit 128. The display unit 130 is, for example, a cathode ray tube (CRT), a liquid crystal display (LCD), or a touch panel-type display. The functions of the manipulation unit 110 and the display unit 130 may be realized by a one touch panel-type display.

The storage unit 140 stores a program or data for performing various calculation processes or control processes by the processing unit 120. The storage unit 140 is used as a working area of the processing unit 120, and is also used to temporarily store the manipulation signal input from the manipulation unit 110, the data acquired from the terahertz wave detection unit 40, and a result of an operation executed according to various programs by the processing unit 120.

1.2. Operation

Figure 9:
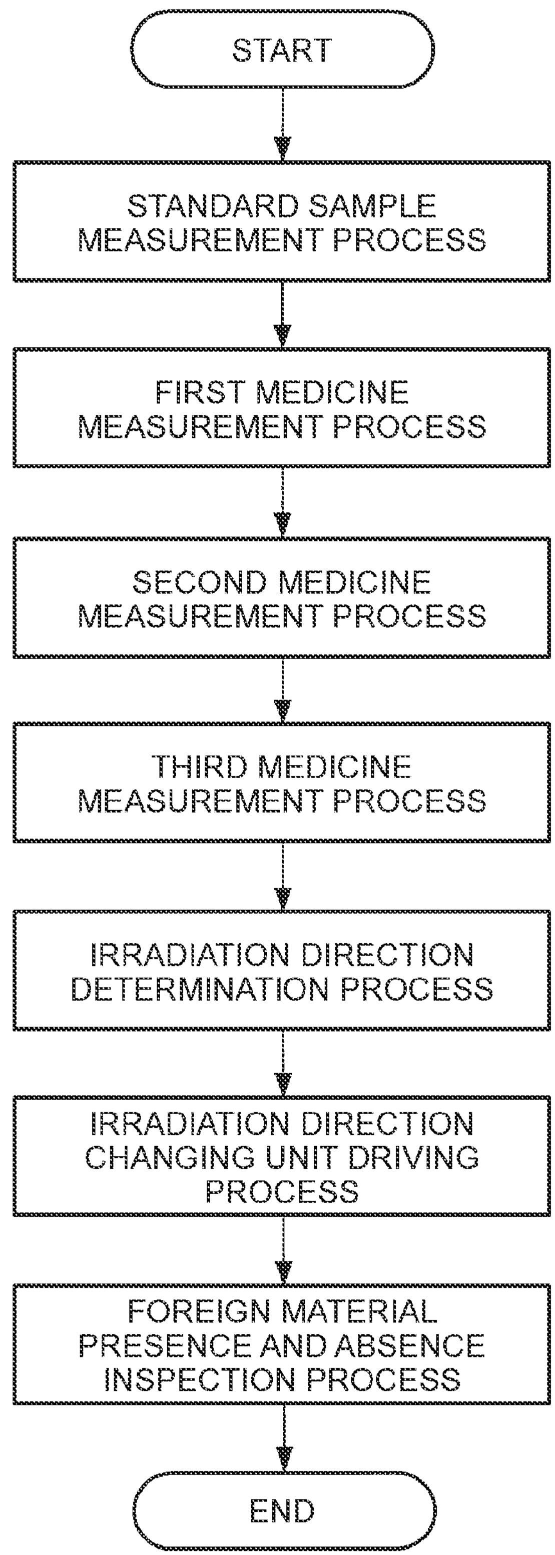
FIG. 9 is a flowchart for illustrating operations of a specimen inspection apparatus according to a first embodiment.

Next, operations of the specimen inspection apparatus 100 will be described with reference to the drawings. FIG. 9 is a flowchart for illustrating the operations of the specimen inspection apparatus 100. FIGS. 10 to 13 are diagrams for illustrating the operations of the specimen inspection apparatus 100. For convenience, in FIGS. 10 to 13, the terahertz wave generation unit 30 and the terahertz wave detection unit 40 are shown in a simplified manner. In FIGS. 10 to 13, an X axis, a Y axis, and a Z axis are shown as three axes intersecting each other. Hereinafter, as the specimen inspection apparatus 100, a configuration of not including the second terahertz wave detection unit 40*b*, that is, a configuration of detecting the terahertz wave transmitting through the medicine 2 will be described.

Figure 10:
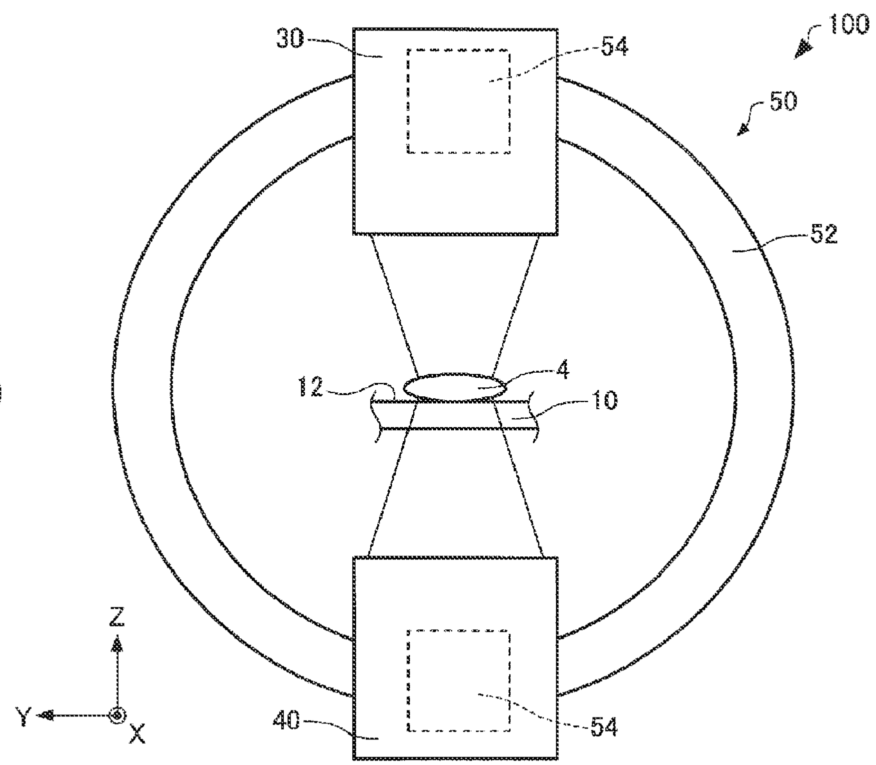
FIG. 10 is a diagram for illustrating operations of a specimen inspection apparatus according to a first embodiment.

First, as shown in FIG. 10, the specimen inspection apparatus 100 performs measurement of a standard sample 4 loaded on the transportation surface 12 (standard sample measurement process). Herein, the "standard sample" is a sample, a terahertz wave of which can be detected without depending on a shape of the sample (at the least less dependent on the shape compared to the case of the medicine 2). That is, a terahertz wave transmitting through the standard sample 4 and is detected by the terahertz wave detection unit 40 has spectra which does not depend on the shape (at the least less dependent on the shape compared to the case of the medicine 2). In detail, the standard sample 4 is a medicine on which printing is not formed.

In detail, as shown in FIG. 1, when the signal S1 is input from the manipulation unit 110, the terahertz wave control unit 122 transmits the driving signal S2 to the terahertz wave generation unit 30. The terahertz wave generation unit 30 emits the terahertz wave towards the standard sample 4 based on the driving signal S2. Then, the terahertz wave detection unit 40 detects the terahertz wave transmitting through the standard sample 4 and transmits the detection signal S3 to the processing unit 120 based on the terahertz wave. In more detail, the detection signal S3 is a signal based on the intensity of the terahertz wave transmitting through the filter 42 of the terahertz wave detection unit 40.

The irradiation direction of the terahertz wave when inspecting the standard sample 4 is not particularly limited, but in the example shown in FIG. 10, the irradiation direction of the terahertz wave is the Z axis direction. As shown in FIG. 1, when the signal S1 is input from the manipulation unit 110, the irradiation direction control unit 126 transmits the driving signal S5 to the irradiation direction changing unit 50. The movable unit 54 of the irradiation direction changing unit 50 is moved based on the driving signal S5 and the irradiation direction of the terahertz wave is set. For example, a gyro sensor (angle sensor) is mounted on the terahertz wave generation unit 30 and the terahertz wave detection unit 40, and the irradiation direction control unit 126 may recognize the position of the movable unit 54 (that is, the terahertz wave generation unit 30 and the terahertz wave detection unit 40) by a signal from the gyro sensor.

Figure 11:
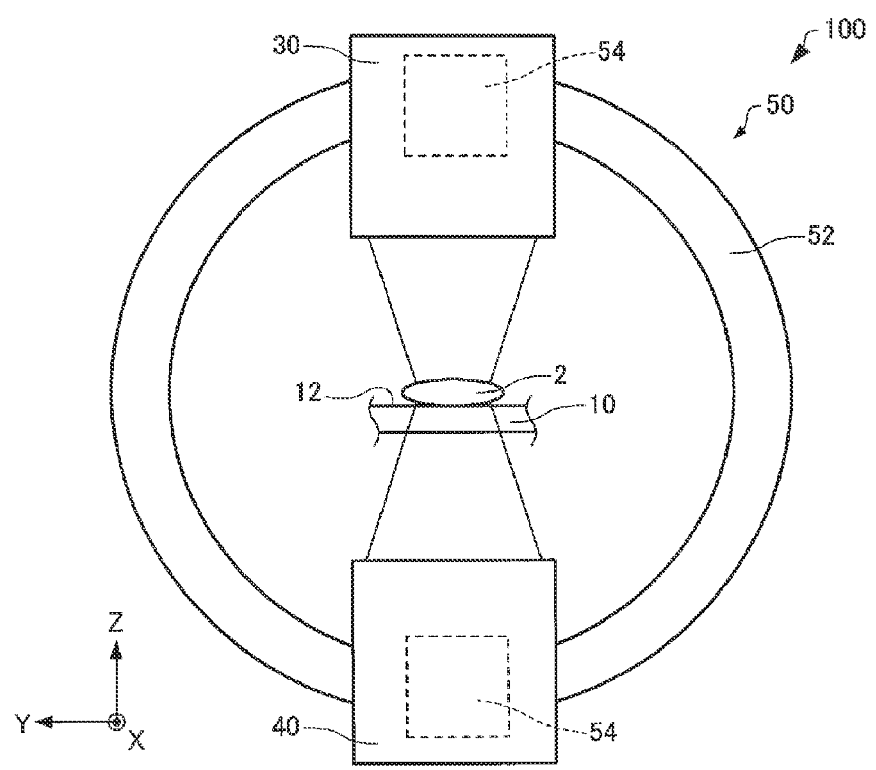
FIG. 11 is a diagram for illustrating operations of a specimen inspection apparatus according to a first embodiment.

Next, as shown in FIG. 11, the specimen inspection apparatus 100 performs measurement of the medicine 2 (medicine 2 on which printing is formed) loaded on the transportation surface 12 (first medicine measurement process). In the process, the irradiation direction of the terahertz wave is not particularly limited, but in the example shown in FIG. 11, the irradiation direction thereof is the Z axis direction (first direction) which is the same as in the standard sample measurement process. The terahertz wave detection unit 40 transmits the detection signal S3 to the processing unit 120 based on the terahertz wave transmitting through the medicine 2.

Figure 12:
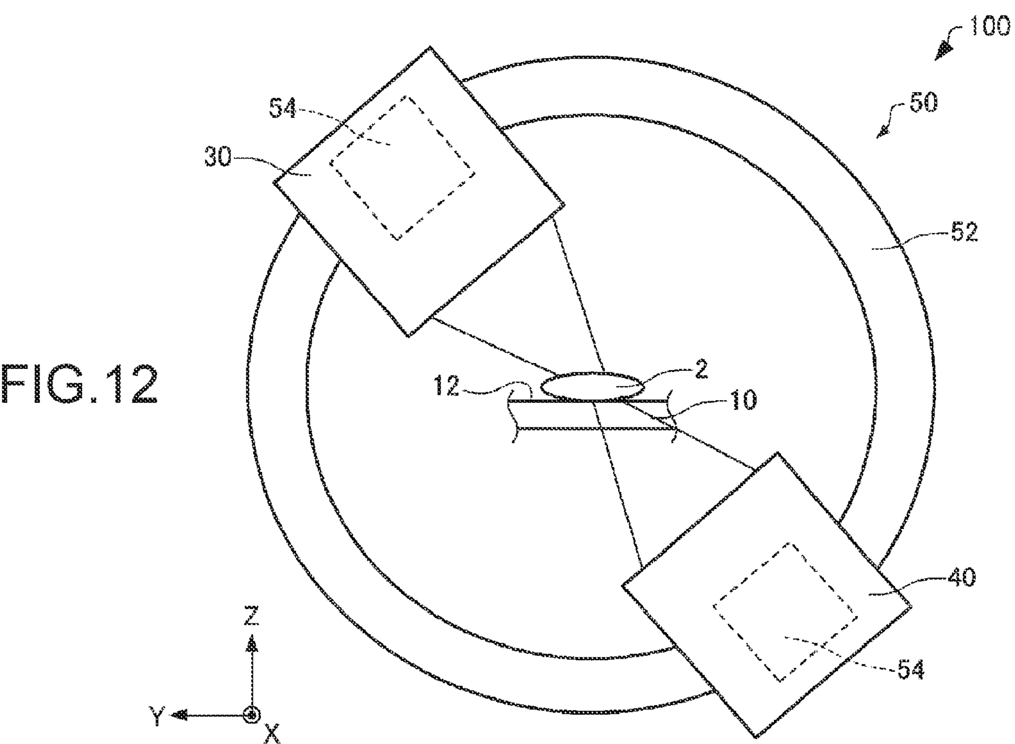
FIG. 12 is a diagram for illustrating operations of a specimen inspection apparatus according to a first embodiment.

Next, as shown in FIG. 12, the specimen inspection apparatus 100 performs measurement of the medicine 2 which is subjected to the measurement in the first medicine measurement process, by changing the irradiation direction of the terahertz wave (second medicine measurement process). In detail, as shown in FIG. 1, the movable unit 54 of the irradiation direction changing unit 50 is moved to a predetermined position based on the driving signal S5 input from the irradiation direction control unit 126. Then, the terahertz wave generation unit 30 emits the terahertz wave towards the medicine 2 based on the driving signal S2 input from the terahertz wave control unit 122. The terahertz wave detection unit 40 transmits the detection signal S3 to the processing unit 120 based on the terahertz wave transmitting through the medicine 2. In the example shown in FIG. 12, the irradiation direction of the terahertz wave is a direction (second direction) which is tilted by 45° with respect to the Z axis.

Figure 13:
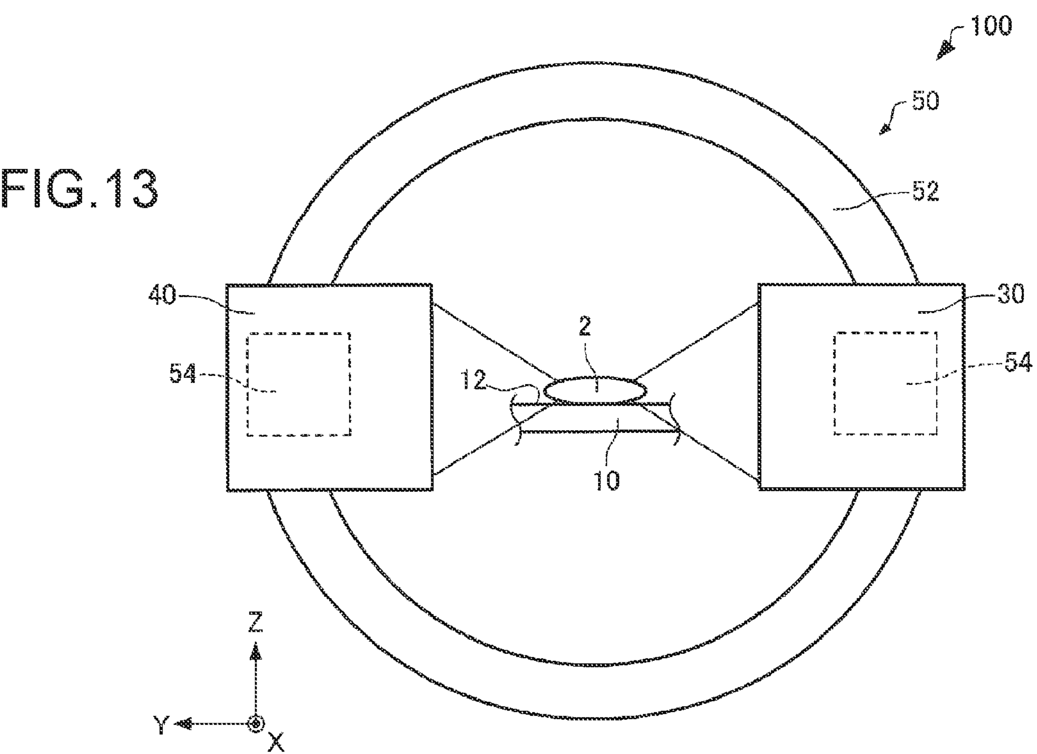
FIG. 13 is a diagram for illustrating operations of a specimen inspection apparatus according to a first embodiment.

Next, as shown in FIG. 13, the specimen inspection apparatus 100 performs measurement of the medicine 2 which is subjected to the measurement in the second medicine measurement process, by changing the irradiation direction of the terahertz wave (third medicine measurement process). In the example shown in FIG. 13, the irradiation direction of the terahertz wave is a direction (X axis direction, third direction) which is tilted by 90° with respect to the Z axis. The specific operations of the irradiation direction changing unit 50 of this process are the same as the operations in the second medicine measurement process described above.

In the second and third medicine measurement processes, the transmission of the driving signals S2 and S5 may be performed according to the signal S1 from the manipulation unit 110 or may be performed according to the program stored in the storage unit 140.

In addition, the transportation unit 10 stops at the start of the measurement of the first medicine measurement process until the end of the measurement of the third medicine measurement process. The stop of the transportation unit 10 may be performed based on the signal input to the transportation unit 10 from the processing unit 120.

Next, the specimen inspection apparatus 100 determines the irradiation direction based on the terahertz wave detected by the terahertz wave detection unit 40 (irradiation direction determination process). In detail, as shown in FIG. 1, the irradiation direction determination unit 124 determines a terahertz wave having intensity which is closest to that of the terahertz wave detected in the standard sample measurement process, among the terahertz waves detected in the first to third medicine measurement processes, based on the detection signal S3 input from the terahertz wave detection unit 40 to determine the irradiation direction. Hereinafter, the process will be described more specifically.

Figure 14:
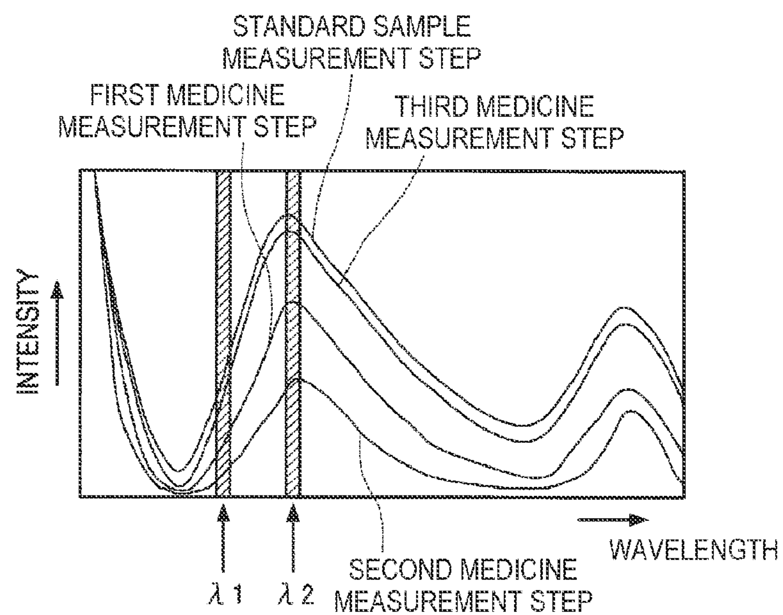
FIG. 14 is a graph showing spectra of a specimen and a standard sample as inspection objects in a terahertz band.

FIG. 14 is a graph showing spectra of the medicine 2 and the standard sample 4 in a terahertz band. λ1 shown in FIG. 14 is, for example, a wavelength passing through the first region 431 of the pixel 43 of the filter 42 of the terahertz wave detection unit 40, and λ2 is a wavelength passing through the second region 432 of the pixel 43 (see FIG. 6). In the example shown in FIG. 14, the terahertz wave detected in the third medicine measurement process has both, intensity of a component of the wavelength λ1 and intensity of a component of the wavelength λ2 of the detected terahertz wave, which are closest to those of the terahertz wave detected in the standard sample measurement process. Accordingly, the irradiation direction determination unit 124 determines a direction (third direction) in which the terahertz wave is emitted in the third medicine measurement process, as an irradiation direction of the terahertz wave in a foreign material presence and absence inspection process which will be described later.

In the example shown in FIG. 14, the irradiation direction determination unit 124 compares the intensity of components of two types of wavelengths using the first region 431 and the second region 432 of the pixel 43, but may determine the irradiation direction of the terahertz wave by comparing the intensity of the component of one type of the wavelength. However, in a case of comparing the intensity of the component of one type of the wavelength, if foreign materials are contained in the medicine 2 inspected in the first to third medicine measurement processes, it is difficult to determine whether a value of the intensity of the terahertz wave is a result from the foreign materials or from the irradiation direction. Accordingly, as the example shown in FIG. 14, it is preferable to compare the intensity of components of two or more types of wavelengths.

Next, the specimen inspection apparatus 100 drives the irradiation direction changing unit 50 based on the determination of the irradiation direction determination unit 124 (irradiation direction changing unit driving process). In detail, as shown in FIG. 1, the irradiation direction determination unit 124 transmits the signal S4 based on the determination of the irradiation direction of the terahertz wave, to the irradiation direction changing unit 50. The irradiation direction control unit 126 transmits the driving signal S5 to the irradiation direction changing unit 50 based on the signal S4 input from the irradiation direction determination unit 124. The movable unit 54 of the irradiation direction changing unit 50 is driven based on the driving signal S5 input from the irradiation direction control unit 126.

As described above, in a case where the irradiation direction (specifically the third direction) determined by the irradiation direction determination unit 124 is the same as the irradiation direction in the medicine measurement process (specifically third medicine measurement process) lastly performed among the first to third medicine measurement processes, the movable unit 54 does not move.

Next, the specimen inspection apparatus 100 emits the terahertz wave from the irradiation direction determined by the irradiation direction determination unit 124 to inspect the medicine 2 (foreign material presence and absence inspection process). In this process, the transportation unit 10 is driven and presence or absence of the foreign materials is inspected with respect to the medicine 2 other than the medicine 2 measured in the first to third medicine measurement processes. In the process, the plurality of medicines 2 can be inspected. In the process, spectroscopic imaging of the medicine 2 is performed.

Figure 15:
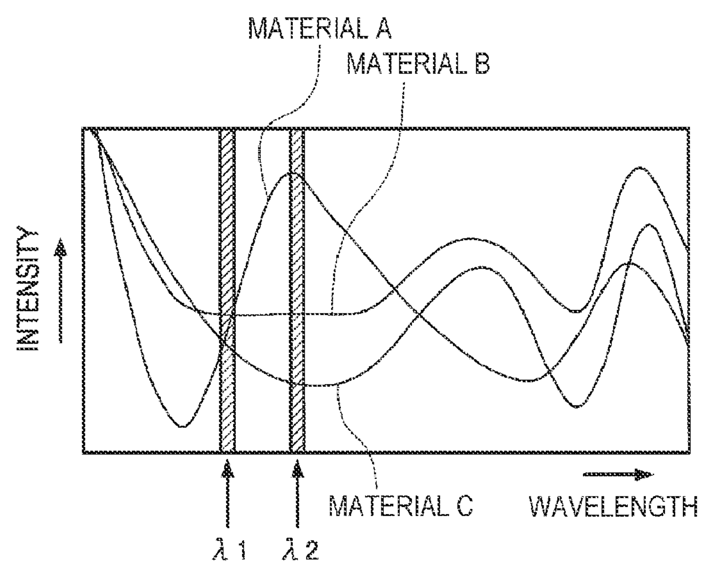
FIG. 15 is a graph showing spectra of a specimen as an inspection object in a terahertz band.
Figure 16:
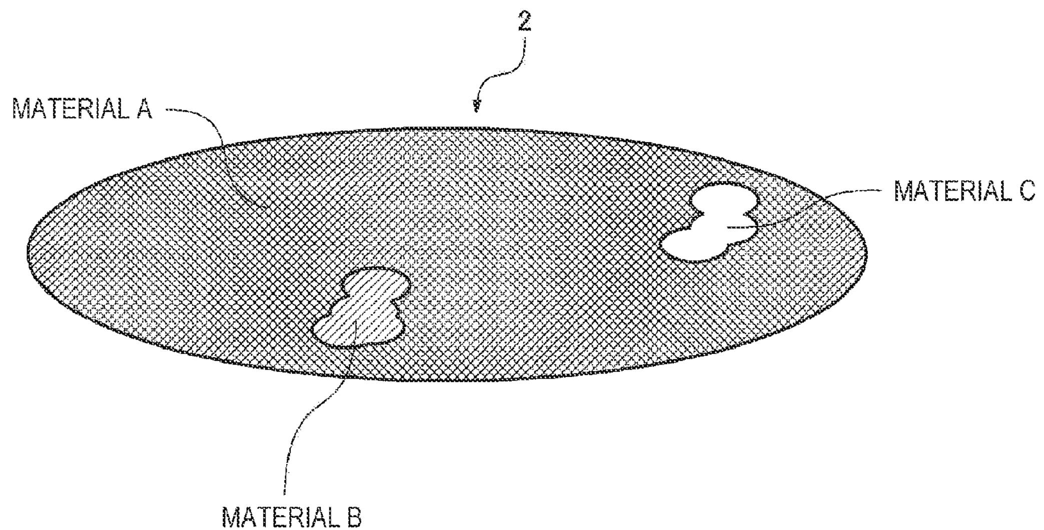
FIG. 16 is a diagram of an image showing distribution of materials A, B, and C of a specimen as an inspection object.

Hereinafter, a case where the medicine 2 is configured with three materials A, B, and C (materials B and C are foreign materials) will be described in detail. FIG. 15 is a graph showing spectra of the medicine 2 in a terahertz band. FIG. 16 is a diagram of an image showing distribution of the materials A, B, and C of the medicine 2.

As described above, the first region 431 and the second region 432 are used in the pixel 43 of the filter 42 of the terahertz wave detection unit 40 (see FIG. 6). When a pass wavelength of the first region 431 is set to λ1, a pass wavelength of the second region 432 is set to λ2, intensity of the component at the wavelength λ1 of the terahertz wave transmitting through the medicine 2 is set to al, and intensity of the component at the wavelength $\lambda 2$ thereof is set to $\alpha 2$, the pass wavelength $\lambda 1$ of the first region 431 and the pass wavelength $\lambda 2$ of the second region 432 are set so that differences ($\alpha 2-\alpha 1$) between the intensity $\alpha 2$ and the intensity $\alpha 1$ can be significantly differentiated between the material A, the material B, and the material C.

As shown in FIG. 15, in the material A, the difference ($\alpha 2-\alpha 1$) between the intensity $\alpha 2$ of the component at the wavelength $\lambda 2$ and the intensity $\alpha 1$ of the component at the wavelength $\lambda 1$ of the terahertz wave transmitting through the medicine 2 is a positive value. In the material B, the difference ($\alpha 2-\alpha 1$) between the intensity $\alpha 2$ and the intensity $\alpha 1$ is zero. In the material C, the difference ($\alpha 2-\alpha 1$) between the intensity $\alpha 2$ and the intensity $\alpha 1$ is a negative value.

The terahertz wave detection unit 40 detects the intensity $\alpha 1$ and the intensity $\alpha 2$. The detected results are transmitted to the image forming unit 128 (see FIG. 1). The emission of the terahertz wave to the medicine 2 and the detection of the terahertz wave transmitting through the medicine 2 are performed with respect to all medicines 2.

In the image forming unit 128, the difference ($\alpha 2-\alpha 1$) between the intensity $\alpha 2$ and the intensity al is acquired based on the detected results of the terahertz wave detection unit 40. From the medicine 2, a portion in which the difference ($\alpha 2-\alpha 1$) is a positive value, a portion in which the difference ($\alpha 2-\alpha 1$) is zero, and a portion in which the difference ($\alpha 2-\alpha 1$) is a negative value are determined and specified as the material A, the material B, and the material C, respectively.

In addition, as shown in FIG. 16, the image forming unit 128 creates image data of the image showing the distribution of the materials A, B, and C of the medicine 2. This image data is transmitted to the display unit 130 from the image forming unit 128, and the display unit 130 displays the image showing the distribution of the materials A, B, and C of the medicine 2. For example, the image is displayed by coloring a region with the distribution of the material A of the medicine 2 in black, a region with the distribution of the material B in gray, and a region with the distribution of the material C in white. As described above, in the specimen inspection apparatus 100, the identification of each material configuring the medicine 2 and the distribution measurement of each material thereof can be performed at the same time.

In the example described above, the terahertz wave is emitted from three directions (first to third directions) to determine the irradiation direction in the foreign material presence and absence inspection process, but the terahertz wave may be emitted from two directions or four or more directions to determine the irradiation direction in the foreign material presence and absence inspection process. In the specimen inspection apparatus 100, since the rail 52 of the irradiation direction changing unit 50 is provided in a ring shape on the periphery of the transportation unit 10, the emission of the terahertz wave can be performed from various directions.

In the example described above, the method of determining whether or not the foreign materials are contained in the medicine 2 by performing spectroscopic imaging of the medicine 2 has been described, but the presence or absence of the foreign materials may be determined by determining whether or not the intensity of the component at a specified wavelength (intensity of the terahertz wave transmitting through the medicine 2) is in a predetermined range, without performing the spectroscopic imaging.

The specimen as an inspection object of the specimen inspection apparatus 100 is not limited to the medicine, and may be a food item such as a snack or may be a wafer used in a semiconductor process.

The specimen inspection apparatus 100, for example, has the following characteristics.

In the specimen inspection apparatus 100, the irradiation direction changing unit 50 changes the irradiation direction for irradiating the medicine 2, by changing the position of the terahertz wave generation unit 30. Accordingly, in the specimen inspection apparatus 100, in a case where printing is formed on the medicine 2, for example, it is possible to emit the terahertz wave to the medicine 2 by avoiding the irradiation direction in which the scattering of the terahertz wave is great due to the printing. Thus, the specimen inspection apparatus 100 can suppress the decrease in the detection precision due to the scattering of the terahertz wave and can obtain high detection precision.

The specimen inspection apparatus 100 includes the detection position control unit (irradiation direction control unit) 126 which controls the position of the terahertz wave detection unit 40 so as to detect the terahertz wave according to the irradiation direction of the terahertz wave. Accordingly, the specimen inspection apparatus 100 can obtain high detection precision.

In the specimen inspection apparatus 100, the transportation unit 10 is configured to arrange the medicines 2 so that the medicines 2 are not superimposed on each other, when seen from the irradiation direction of the terahertz wave. Accordingly, it is possible to emit the terahertz waves having the same intensity to each of the plurality of medicines 2.

2. Second Embodiment

Figure 17:
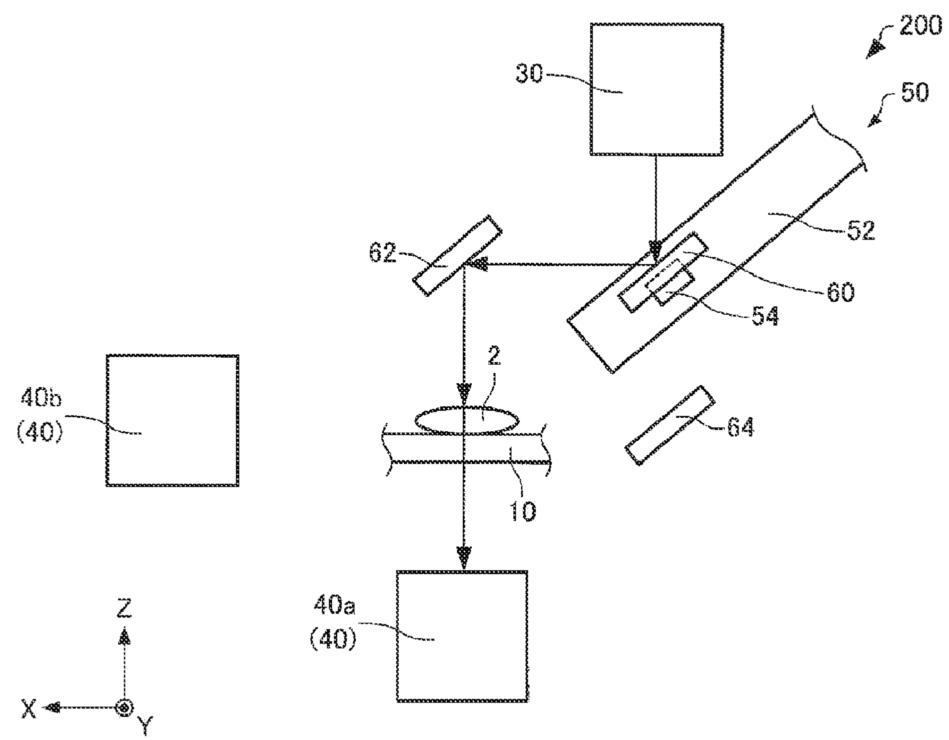
FIG. 17 is a diagram schematically showing a part of a specimen inspection apparatus according to a second embodiment.
Figure 18:
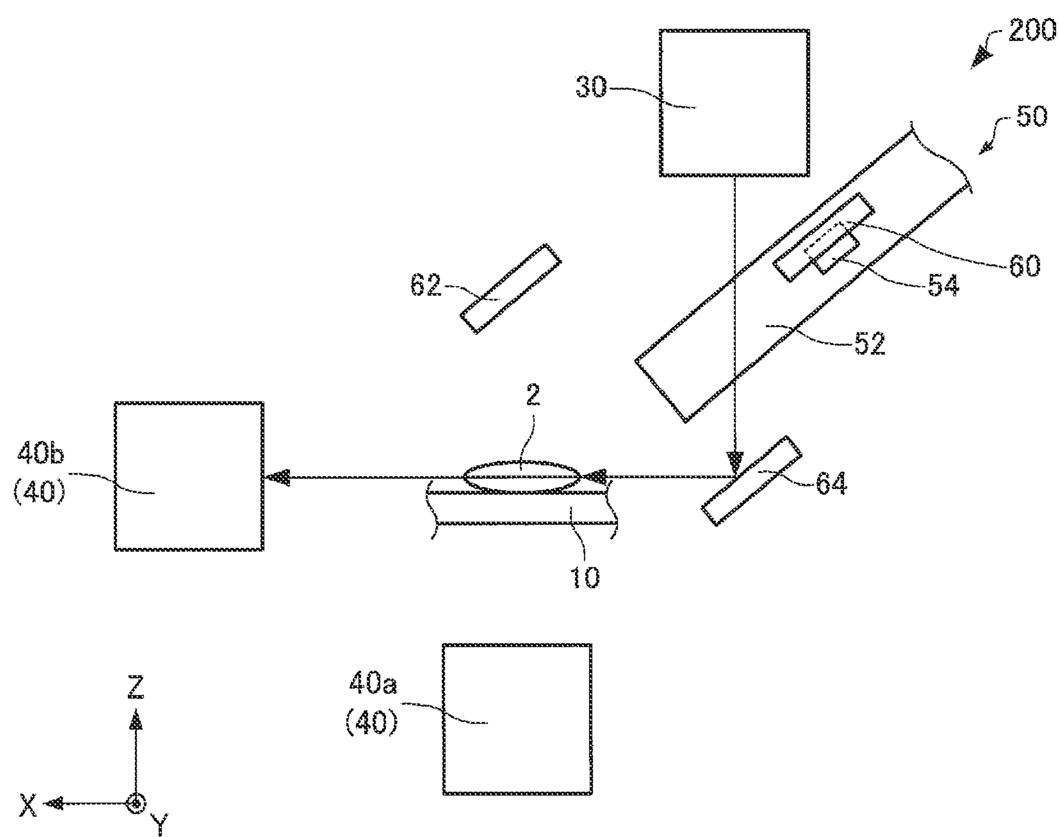
FIG. 18 is a diagram schematically showing a part of a specimen inspection apparatus according to a second embodiment.

Next, a specimen inspection apparatus according to a second embodiment will be described with reference to the drawings. FIGS. 17 and 18 are diagrams schematically showing a part of a specimen inspection apparatus 200 according to the second embodiment. Hereinafter, points of the specimen inspection apparatus 200 according to the second embodiment which are different from the example of the specimen inspection apparatus 100 according to the first embodiment will be described, and the description of the overlapping points will be omitted.

As shown in FIGS. 11 to 13, in the specimen inspection apparatus 100, the irradiation direction changing unit 50 changes the irradiation direction of the terahertz wave by changing the position of the terahertz wave generation unit 30. Meanwhile, as shown in FIGS. 17 and 18, in the specimen inspection apparatus 200, the irradiation direction changing unit 50 includes a first reflection unit 60 which reflects the terahertz wave emitted from the terahertz wave generation unit 30, and changes the irradiation direction of the terahertz wave by changing the position of the first reflection unit 60.

As shown in FIGS. 17 and 18, the specimen inspection apparatus 200 further includes a second reflection unit 62 and a third reflection unit 64. The reflection units 60, 62, and 64 can reflect the terahertz wave. Materials of the reflection units 60, 62, and 64 are glass and metal, for example.

The first reflection unit 60 is supported by the movable unit 54 of the irradiation direction changing unit 50. Accordingly, the first reflection unit 60 is movable according to the movement of the movable unit 54. In the example shown in the drawings, the rail 52 of the irradiation direction changing unit 50 is provided in a linear shape and the first reflection unit 60 can be linearly moved.

The first terahertz wave detection unit 40*a* and the second terahertz wave detection unit 40*b* are provided to be separated from the terahertz wave generation unit 30. In the example shown in the drawings, the first terahertz wave detection unit 40*a* is positioned in the negative Z axis direction of the transportation unit 10, and the transportation unit 10 is positioned between the first terahertz wave detection unit 40*a* and the second reflection unit 62. The second terahertz wave detection unit 40*b* is positioned in the positive X axis direction of the transportation unit 10, and the transportation unit 10 is positioned between the second terahertz wave detection unit 40*b* and the third reflection unit 64.

As shown in FIG. 2, in the specimen inspection apparatus 100, the second terahertz wave detection unit 40*b* has a configuration of including the mirror 48 and not including the second lens 46, but in the specimen inspection apparatus 200, the second terahertz wave detection unit 40*b* has a configuration of including the second lens 46 and not including the mirror 48, in the same manner as the first terahertz wave detection unit 40*a* shown in FIG. 2. In the specimen inspection apparatus 200, both terahertz wave detection units 40*a* and 40*b* detect the terahertz wave transmitting through the medicine 2.

In the specimen inspection apparatus 100, the terahertz wave generation unit 30 has a configuration of including the half mirror 37, but in the specimen inspection apparatus 200, the terahertz wave generation unit 30 has a configuration of not including the half mirror 37.

In the specimen inspection apparatus 200, as shown in FIG. 17, in the first medicine measurement process, the reflection units 60 and 62 reflect the terahertz wave emitted from the terahertz wave generation unit 30 towards the medicine 2. The terahertz wave which is emitted to and transmitted through the medicine 2 is detected by the first terahertz wave detection unit 40*a*. The irradiation direction in the first medicine measurement process is the Z axis direction (first direction).

The "irradiation direction" is a travelling direction of the terahertz wave immediately before reaching the medicine 2. That is, in a case where the terahertz wave emitted from the terahertz wave generation unit 30 reaches the medicine 2 by changing the travelling directions by passing through the plurality of reflection units, the irradiation direction is a direction to the medicine 2 from the reflection unit which the terahertz value lastly approaches. In the example shown in FIG. 17, the irradiation direction is a direction to the medicine from the second reflection unit 62, that is, the Z axis direction.

Next, in the specimen inspection apparatus 200, as shown in FIG. 18, in the second medicine measurement process, the movable unit 54 of the irradiation direction changing unit 50 is moved from the position thereof in the first medicine measurement process. Accordingly, the terahertz wave emitted from the terahertz wave generation unit 30 is reflected by the third reflection unit 64 to be emitted to the medicine 2, without being reflected by the first reflection unit 60. That is, the irradiation direction changing unit 50 changes the irradiation direction of the terahertz wave by changing the position of the first reflection unit 60. The terahertz wave which is emitted to and transmitted through the medicine 2 is detected by the second terahertz wave detection unit 40*b*. The irradiation direction in the second medicine measurement process is the X axis direction (second direction).

Next, in the same manner as the specimen inspection apparatus 100, the specimen inspection apparatus 200 determines whether to set the first direction or the second direction as the irradiation direction in the foreign material presence and absence inspection process, based on the measured results in the first and second medicine measurement processes.

In the specimen inspection apparatus 200, by moving the small-sized first reflection unit 60 without moving the terahertz wave generation unit 30 and the terahertz wave detection unit 40, it is possible to easily suppress the decrease in the detection precision due to the scattering of the terahertz wave.

The invention includes substantially the same configuration as the configuration described in the embodiments (for example, configuration having the same functions, methods, and results, or configuration having the same object and effects). The invention includes a configuration obtained by replacing the non-essential parts of the configuration described in the embodiments. The invention includes a configuration for realizing the same operation results or a configuration for obtaining the same object as the configuration described in the embodiments. The invention includes a configuration obtained by adding the related art to the configuration described in the embodiments.

The entire disclosure of Japanese Patent Application No. 2013-046264, filed Mar. 8, 2013 is expressly incorporated by reference herein.

What is claimed is:

1. A specimen inspection apparatus comprising:

a terahertz wave generation unit which generates and emits a terahertz wave to a particular specimen of specimens as inspection objects;

a transportation unit which includes a transportation surface on which the specimens are loaded and transported in an in-plane direction of the transportation surface;

an irradiation direction changing unit configured to change an irradiation direction of the terahertz wave emitted from the terahertz wave generation unit to the particular specimen loaded on the transportation surface; and a terahertz wave detection unit which detects the terahertz wave emitted to the particular specimen loaded on the transportation surface and determines a detection result, wherein, based on the detection result, the irradiation direction changing unit changes the irradiation direction by moving the terahertz wave generation unit to another position at which the particular specimen is irradiated by the terahertz wave generation unit detected by the terahertz wave detection unit.

2. The specimen inspection apparatus according to claim 1, further comprising:

a detection position control unit which controls a position of the terahertz wave detection unit so as to detect the terahertz wave along the irradiation direction.

3. The specimen inspection apparatus according to claim 1, wherein the transportation unit is configured so as to arrange the specimens so that the specimens are not superimposed on each other when seen from the irradiation direction.

4. The specimen inspection apparatus according to claim 1, wherein the terahertz wave generation unit includes an optical pulse generation unit which generates an optical pulse, and a photoconductive antenna which is irradiated with the optical pulse generated by the optical pulse generation unit.

5. A specimen inspection apparatus comprising:

a terahertz wave generation unit which generates and emits a terahertz wave to particular specimen of specimens as inspections objects;

a transportation unit which includes a transportation surface on which the specimens are loaded and transported in an in-plane direction of the transportation surface;

an irradiation direction changing unit configured to change an irradiation direction of the terahertz wave emitted from the terahertz wave generation unit to the particular specimen loaded on the transportation surface; and a terahertz wave detection unit which detects the terahertz wave emitted to the particular specimen loaded on the transportation surface and determines a direction result, wherein the irradiation direction changing unit includes a reflection units which can reflect the terahertz wave emitted from the terahertz wave generation unit, and, based on the detection result, changes the irradiation direction by putting the reflection unit in or out of a path of the terahertz wave.

6. The specimen inspection apparatus according to claim 5, wherein the transportation unit is configured so as to arrange the specimens so that the specimens are not superimposed on each other when seen from the irradiation direction.

7. The specimen inspection apparatus according to claim 5, wherein the terahertz wave generation unit includes an optical pulse generation unit which generates an optical pulse, and a photoconductive antenna which is irradiated with the optical pulse generated by the optical pulse generation unit.

* * * * *